United States Patent
Huang

(10) Patent No.: US 10,485,907 B2
(45) Date of Patent: Nov. 26, 2019

(54) PORTABLE NEGATIVE-PRESSURE DEVICE

(71) Applicant: BenQ Materials Corporation, Taoyuan (TW)

(72) Inventor: Mao-Sung Huang, Taoyuan (TW)

(73) Assignee: BenQ Materials Corporation, Taoyuan (TW)

(*) Notice: Subject to any disclaimer, the term of this patent is extended or adjusted under 35 U.S.C. 154(b) by 356 days.

(21) Appl. No.: 15/427,041

(22) Filed: Feb. 7, 2017

(65) Prior Publication Data

US 2017/0326277 A1    Nov. 16, 2017

(30) Foreign Application Priority Data

May 10, 2016   (TW) .............................. 105114439 A

(51) Int. Cl.
| | |
|---|---|
| *A61M 1/00* | (2006.01) |
| *A61L 26/00* | (2006.01) |
| *A61M 27/00* | (2006.01) |
| *A61F 13/00* | (2006.01) |
| *A61F 13/02* | (2006.01) |
| *A61F 15/00* | (2006.01) |

(52) U.S. Cl.
CPC .......... *A61M 1/009* (2014.02); *A61L 26/0052* (2013.01); *A61M 1/0043* (2013.01); *A61L 2430/34* (2013.01); *A61M 2205/3337* (2013.01); *A61M 2205/3344* (2013.01)

(58) Field of Classification Search
CPC .......... A61M 1/00; A61M 27/00; A61F 13/00; A61F 13/02; A61F 15/00
See application file for complete search history.

(56) References Cited

U.S. PATENT DOCUMENTS

| | | | | |
|---|---|---|---|---|
| 6,174,306 B1 * | 1/2001 | Fleischmann | ........ | A61B 17/085 604/540 |
| 8,216,198 B2 * | 7/2012 | Heagle | ................ | A61M 1/0001 604/313 |
| 8,298,200 B2 * | 10/2012 | Vess | .................... | A61M 1/0023 604/313 |
| 2014/0276489 A1 * | 9/2014 | Robinson | .......... | A61F 13/00068 604/319 |
| 2015/0018784 A1 * | 1/2015 | Coulthard | ........... | A61M 1/0035 604/319 |

FOREIGN PATENT DOCUMENTS

| | | |
|---|---|---|
| CN | 101917947 A | 12/2010 |
| CN | 202236537 U | 5/2012 |
| CN | 103987410 A | 8/2014 |
| CN | 105546169 A * | 1/2016 |
| TW | 286285 B | 9/1996 |

* cited by examiner

*Primary Examiner* — Tatyana Zalukaeva
*Assistant Examiner* — Ilya Y Treyger
(74) *Attorney, Agent, or Firm* — CKC & Partners Co., LLC

(57) ABSTRACT

A portable negative-pressure device including a housing, a piston, a barrier layer and a spring means for forming a first collection chamber and a second collection chamber having a variable volume to form a pressure-reducing region is provided. In the situation of that the exudates have been stored in the first collection chamber, the portable negative-pressure device can still maintain a sufficient negative pressure by continuously compressing the piston, and the second collection chamber will provide an additional liquid storage space.

13 Claims, 10 Drawing Sheets

PORTABLE NEGATIVE-PRESSURE DEVICE

RELATED APPLICATIONS

This application claims the priority benefit of Taiwanese application serial no. 105114439, filed on May 10, 2016, which is incorporated herein by reference.

BACKGROUND

Technical Field

The present disclosure relates to a portable negative-pressure device for providing negative-pressure to a negative-pressure wound dressing. Particularly, the present disclosure relates to a portable negative-pressure device suitably for generating negative-pressure manually.

Description of Related Art

The human body's wound healing is an intricate process after the body tissues gets injured. At the very beginning, various proteins and the blood-clotting materials for wound healing approach the wound area via blood to cause haemostatic mechanism; that is, the formation of blood clotting prevents further bleeding, and the phagocytes engulf dead cells along with bacteria, pathogens and/or debris from the damage. Then, the wound healing enters the proliferation phase. The wound starts to repair itself and is rebuilt with new fibroblast and granulation tissue around the wound area. The granulation tissue forms and the wound contracts to close the wound area. Finally, the closed wound area grows with scar tissue over time.

The common wound dressing treats the wound by physically absorbing the wound exudates to keep the wound area dry. However, the common wound dressing is unable to control the humidity surrounding the wound area, and the wound healing will be adversely effected due to the over dry condition around the wound area.

Negative-pressure wound therapy (NPWT) is a therapeutic technique utilizing humidity control of a wound in the proliferation phase thereof to promote the intricate process of the wound healing. The negative-pressure wound therapy is typically using a negative-pressure source, such as a vacuum pump in connection with an airtight seal, suction member and biocompatible porous dressing to generate a negative-pressure environment around the wound area to drainage the excess wound fluids and exudates, encourage the migration of the healthy tissue, maintain moisture in the surrounding tissue and increase the blood flow to accelerate the wound healing. The negative-pressure wound therapy utilizing the intricate process of wound healing can effectively promote the blood flow to the wound area, stimulate the formation of granulation tissue and encourage the migration of healthy tissue over the wound. The negative-pressure wound therapy removes the exudates from the wound tissue to inhibit the bacterial growth.

The common systems for using in negative-pressure wound therapy mainly have two types: one is a system with a fluid storage container and the other is a system with an absorptive wound dressing. The two types both need an additional negative-pressure source which is usually an electric pump. However, it is not convenient because of the requirement of a large motor structure of the electric pump and an additional electric source. Especially, when using the system with a fluid storage container, the system constructs with an additional fluid storage container and conduits, and the system restricts patient's mobility. When using the system with absorptive wound dressing, the absorptive wound dressing, which is limited by the less amount of exudates absorption, needs to be replaced more frequently, and changing the dressing will make patients uncomfortable.

Accordingly, there is a demand of a novel portable negative-pressure device for suitably using along with a negative-pressure wound therapy system. The novel portable negative-pressure device is used more easily and conveniently than the one used with a canister. In addition, the novel portable negative-pressure device can provide much collection volume for exudates than the one used with an absorptive wound dressing.

SUMMARY

In accordance with the above-mentioned, the present disclosure provides a portable negative-pressure device, which can generate negative-pressure manually for using with a negative-pressure wound dressing.

The present disclosure provides a portable negative-pressure device for using with a negative-pressure wound dressing comprising a housing having an open end and a closed end, wherein the closed end has an exudates inlet having a first check valve and connecting to the negative-pressure wound dressing via a delivery tube; a piston disposed at the open end of the housing, wherein the piston has an exhaust port configured by a second check valve and an air-permeable waterproof structure; a barrier layer disposed in the housing to divide the housing into two collection chambers, wherein the first collection chamber has a fixed volume with the closed end, and the second collection chamber has a variable volume varied by the position of the piston. The barrier layer has a passage with a third check valve to fluidly communicate the first collection chamber and the second collection chamber, and the first collection chamber comprises a first absorbent material; and a spring means disposed to the piston and configured to form a pressure-reducing region from the compression and resilience back of the piston against the second collection chamber.

In a portable negative-pressure device of one preferred embodiment of the present disclosure, the first collection chamber comprises a porous conduit which is connected to the exudates inlet and extended to the first collection chamber, so that the exudates from the dressing may be uniformly distributed to the first absorbent material of the first collection chamber.

In a portable negative-pressure device of another preferred embodiment of the present disclosure, the porous conduit comprises a manifold structure.

In a portable negative-pressure device of another preferred embodiment of the present disclosure, the second collection chamber comprises a second absorbent material for further absorbing the exudates.

In a portable negative-pressure device of another preferred embodiment of the present disclosure, the first absorbent material and the second absorbent material are selected from a group consisting of sodium polyacrylate, polyacrylamide, polyvinyl alcohol and polyoxyethylene.

In a portable negative-pressure device of another preferred embodiment of the present disclosure, the spring means is selected from a group consisting of a tension spring, a compression spring, a torsion spring and a bending spring.

In a portable negative-pressure device of another preferred embodiment of the present disclosure, the spring means is disposed between the piston and the open end of the housing.

In a portable negative-pressure device of another preferred embodiment of the present disclosure, the spring means is disposed between the piston and the barrier layer.

In a portable negative-pressure device of another preferred embodiment of the present disclosure, the air-permeable waterproof structure comprises an air-permeable waterproof film or liquid absorbing particles.

In a portable negative-pressure device of another preferred embodiment of the present disclosure, the portable negative-pressure device further comprises an auxiliary tool removably disposed at an edge of the housing for pushing the piston sliding toward the barrier layer.

In a portable negative-pressure device of another preferred embodiment of the present disclosure, the portable negative-pressure device further comprises a pressure regulator at the delivery tube between the exudates inlet and the negative-pressure wound dressing.

In a portable negative-pressure device of another preferred embodiment of the present disclosure, the pressure regulator is integrated at the exudates inlet.

In a portable negative-pressure device of another preferred embodiment of the present disclosure, the portable negative-pressure device further comprises a pressure sensor, which is disposed at a side of the housing, interconnecting the first collection chamber and the second collection chamber to indicate the degree of the negative pressure.

The portable negative-pressure device for a negative-pressure wound dressing of the present disclosure can effectively improve the inconvenience caused by the negative-pressure wound therapy system with a fluid storage container, and can provide more collection volume than the negative-pressure wound therapy system with an absorptive wound dressing. Moreover, it is not necessary to interrupt the supply of the negative-pressure source when patients move, and it will not result in inconvenience, pain, or delay of the wound healing time of patients when moving the overall negative-pressure wound therapy system together.

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments. The above and other aspects and advantages of the present disclosure will become apparent from the following detailed description of the present disclosure taken in conjunction with the drawings.

DETAILED DESCRIPTION

Figure 1:
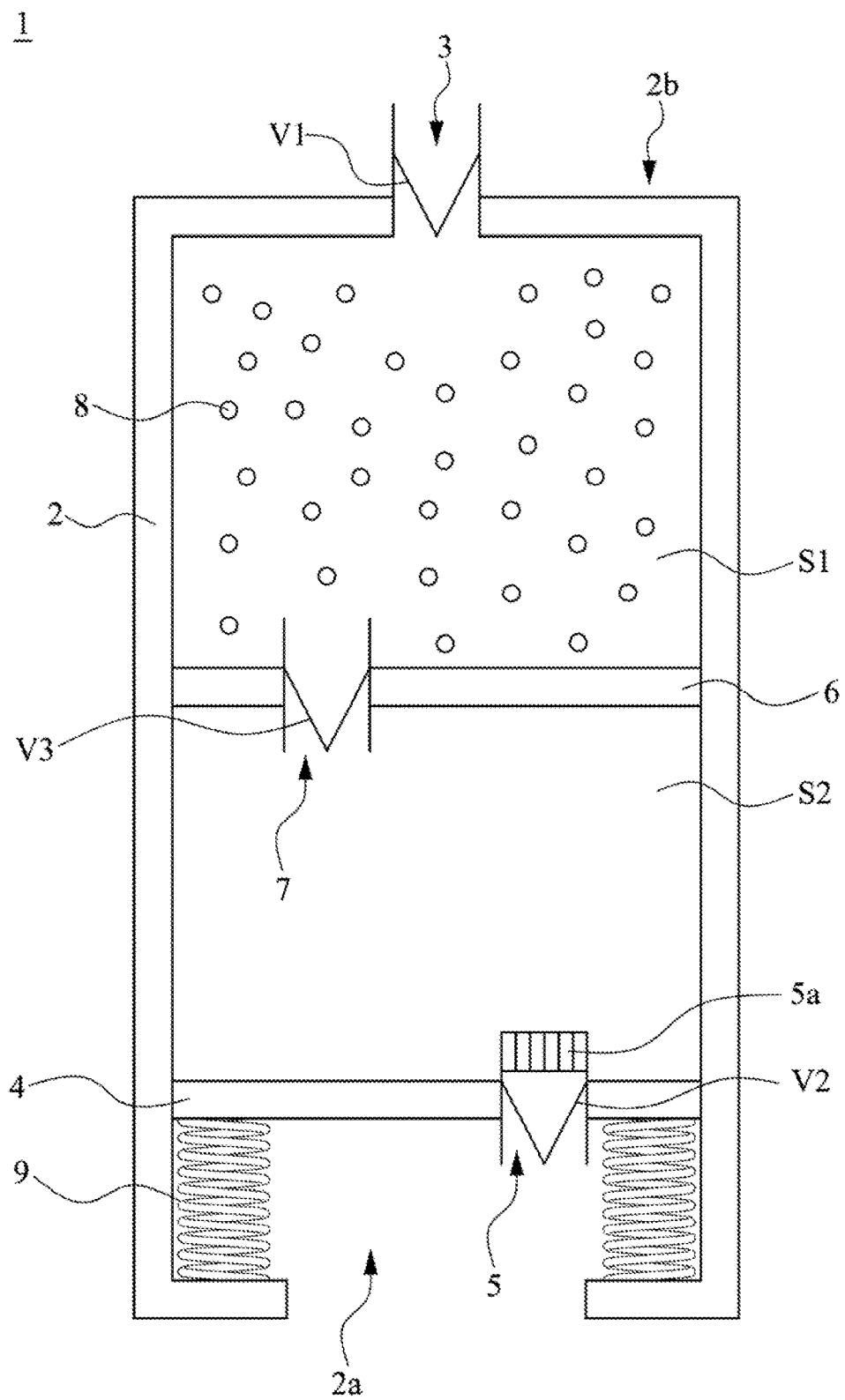
FIG. 1 shows the cross-sectional prospective view of a negative-pressure device in accordance with an embodiment of the present disclosure.

Referring now to the drawings to illustrate the embodiments of the present negative-pressure device. In the following embodiments of the present disclosure, the like elements refer to like symbols in the figures. The following description will introduce the embodiment of the above-described negative-pressure device. For being better understood the embodiments of the present disclosure, a detailed description thereof is provided. However, well-known functions or constructions may not be described in detail for brevity and/or clarity. The drawings are not necessarily to scale, emphasis instead being placed upon illustrating the principles of the disclosure rather than to limit and restrict of the scope of the present disclosure defined in the appended claim.

The advantages and features of the present disclosure will become better understood with reference to the following more detailed description and claims taken in conjunction with the accompanying drawings. It should be understood that the exemplary embodiments of the present disclosure described below may be modified in many different ways without departing from the inventive principles disclosed herein, and the scope of the present disclosure is therefore not limited to these particular embodiments. Rather, these embodiments are provided so that this disclosure will be thorough and complete, and will fully convey the concept of the disclosure to those skilled in the art by way of example and not of limitation. In the drawings, the thickness of layers, films, and regions are exaggerated for clarity. The present disclosure is only defined by the appended claims.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "negative pressure" used herein is referred to the pressure at the wound area is lower than the ambient pressure. In most cases, the negative pressure is lower than the ambient pressure where the patient is located. Alternatively, the negative pressure is lower than a hydrostatic pressure at the wound tissue area. The negative pressure may initially generate fluid flow in the wound tissue area. As the hydrostatic pressure around the tissue area reaches the desired pressure, the flow may slow down, and the pressure then is maintained. Unless otherwise indicated, the pressure value mentioned herein is gauge pressure. Similarly, the increases in negative pressure refer to a decrease in absolute pressure and decreases in negative pressure refer to an increase in absolute pressure.

Referring to FIG. 1, the present disclosure provides a portable negative-pressure device 1 for using with a negative-pressure wound dressing comprising a housing 2 having an open end 2a and a closed end 2b, wherein the closed end 2b has an exudates inlet 3 having a first check valve V1 and connecting to the negative-pressure wound dressing via a delivery tube. A piston 4 movably disposes at the open end 2a of the housing 2, wherein the piston 4 has an exhaust 5 configured by a second check valve V2 and an air-permeable waterproof structure 5a. A barrier layer 6 disposes in the housing 2 for forming a first collection chamber S1 having a fixed volume with the closed end 2b, and forming a second collection chamber S2 having a variable volume varied by the position of the piston 4, wherein the barrier layer 6 has a passage 7 with a third check valve V3 connected the first collection chamber S1 and the second collection chamber S2, and the first collection chamber S1 comprises a first absorbent material 8. A spring means 9 sets to the piston 4, so that the second collection chamber S2 can be compressed to extrude air through the second check valve V2, and released to constitute a pressure-reducing region to attract the exudates into the first collection chamber S1.

In a preferred embodiment of the present disclosure, when using the present negative pressure device, a wound dressing covered a wound area is connected to the negative pressure device 1 via a delivery tube (not shown). The piston 4 is pushed toward the barrier layer 6 to force out the air in the second collection chamber S2 via the check valve V2 and compress the space thereof, as shown in FIG. 3. When the piston 4 is released, the negative pressure phase in the second collection chamber S2 will cause the exudates over the wound to be drawn to the first collection section S1. As the using time goes on, the exudates in the first collection chamber S1 are gradually increased, and the pressure in the portable negative-pressure device 1 is increased with the increasing exudates, the piston 4 can be re-pushed continuously to compress the second collection chamber S2 for maintaining the negative-pressure degree in the portable negative-pressure device 1. In addition, when the first collection chamber S1 is filled with the exudates, the second collection chamber S2 may also provide as an additional storage space for the exudates. Different from the conventional negative-pressure device with only a single collection chamber, the single collection chamber also act as a pressure-reducing region. As the exudates increases, the pressure-reducing region which is compressed to form a negative pressure may be reduced, and the negative pressure will gradually be insufficient, even to compress the remaining pressure-reducing region repeatedly.

Figure 2:
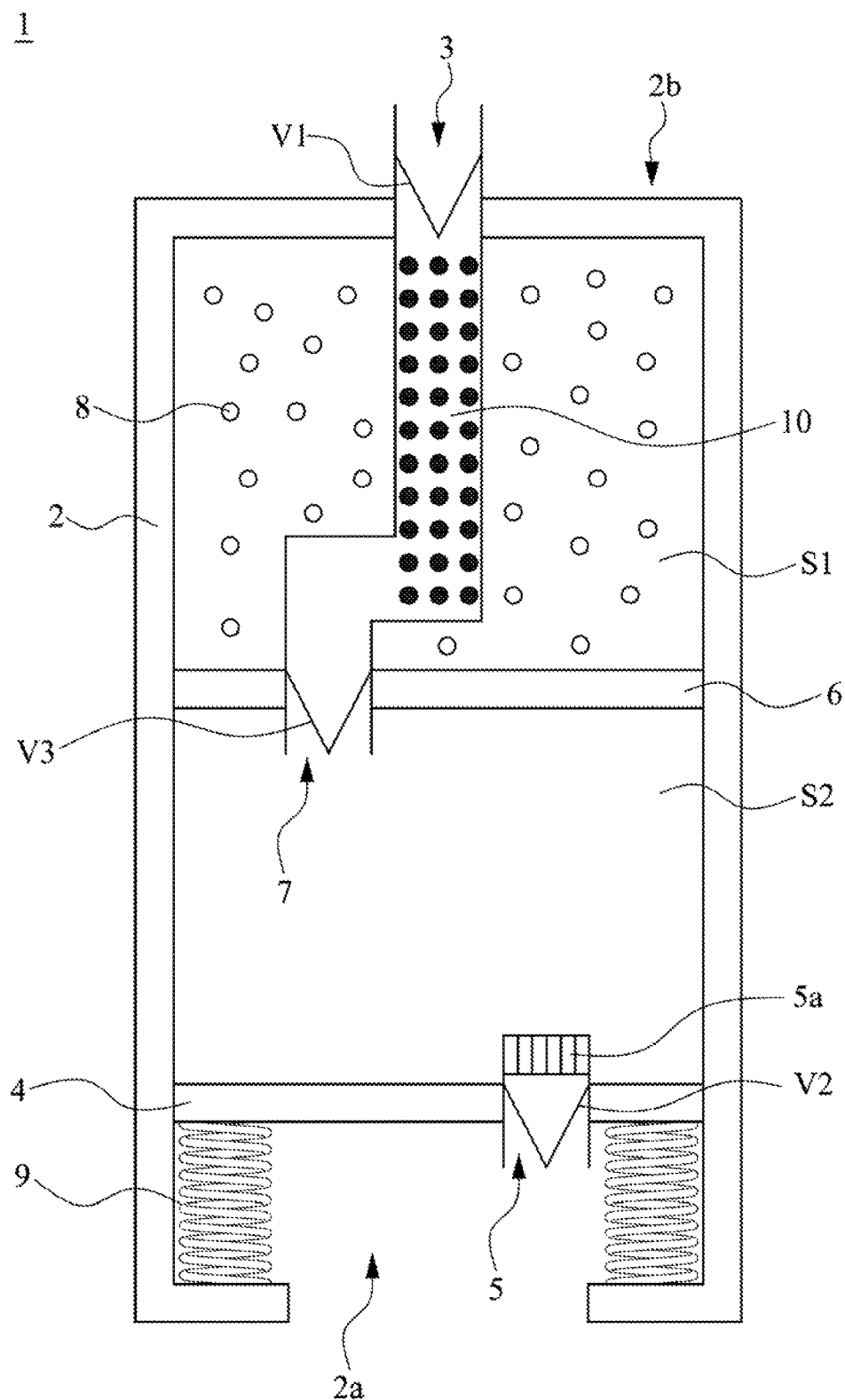
FIG. 2 shows a negative-pressure device in accordance with another embodiment of the present disclosure.

Referring to FIG. 2, in a portable negative-pressure device of one preferred embodiment of the present disclosure, the first collection chamber S1 comprises a porous conduit 10 which is connected to the exudates inlet 3 and extended to the first collection chamber S1, so that the exudates from the dressing can be uniformly distributed to the first absorbent material 8 in the first collection chamber S1.

In a portable negative-pressure device of another preferred embodiment of the present disclosure, the porous conduit 10 comprises a manifold structure with a wide distribution of pores. Therefore, even the first absorbent material 8 has absorbed the exudates that are excessively concentrated and hard to spread, the pores of the porous conduit 10 may not be blocked. The manifold structure of the porous conduit 10 is able to enhance to spread the exudates to the first absorbent material 8, and the excess exudates can easily flow to the second collection chamber S2 which is as a pressure-reducing region.

In a portable negative-pressure device of another preferred embodiment of the present disclosure, the second collection chamber S2 comprises a second absorbent material for further absorbing and catching the exudates flowed into the second collection chamber S2. The first absorbent material of the first collection chamber S1 and the second absorbent material of the second collection chamber S2 may be in the forms of particles filled the housing 2 or coating layers coated on the wall of the housing 2.

In a portable negative-pressure device of another preferred embodiment of the present disclosure, the first absorbent material and the second absorbent material are selected from a group consisting of sodium polyacrylate, polyacrylamide, polyvinyl alcohol, and polyoxyethylene, and can be the same or different.

Figure 3A:
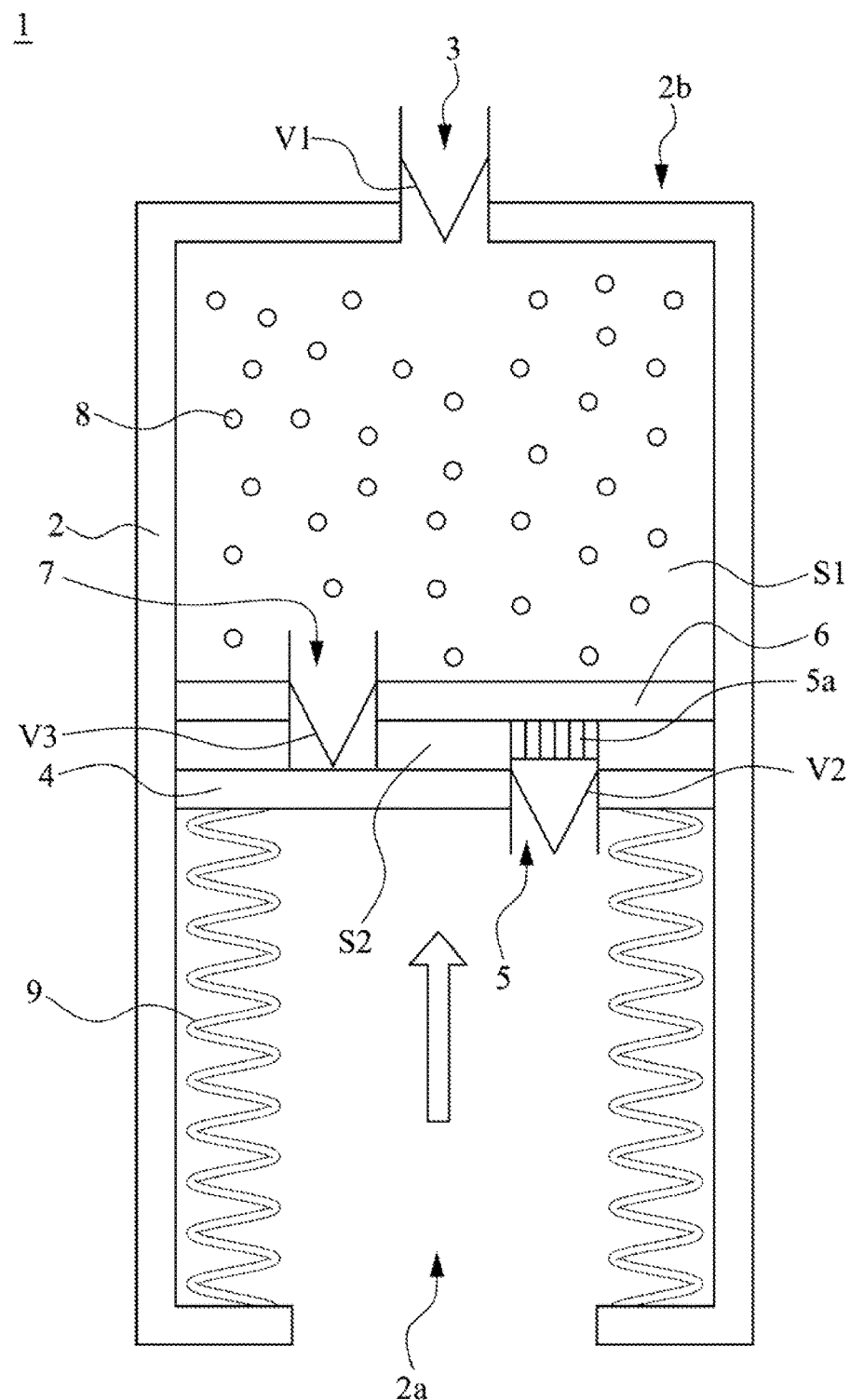
FIG. 3a and FIG. 3b illustrate the principle of a negative-pressure device for forming a negative-pressure source in accordance with an embodiment of the present disclosure.
Figure 3B:
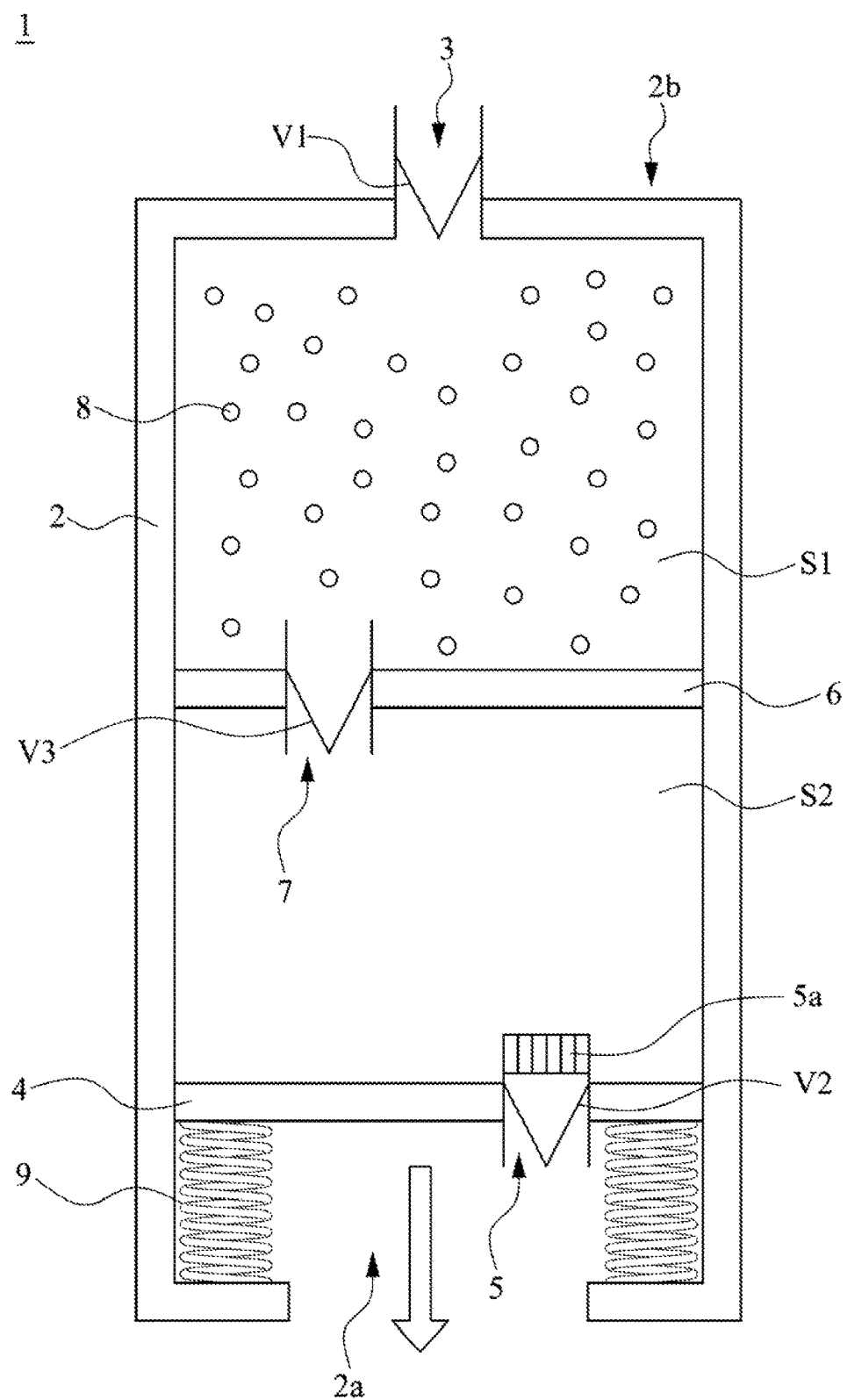

Referring to FIG. 3a and FIG. 3b, in a portable negative-pressure device of another preferred embodiment of the present disclosure, the spring means 9 is disposed between the piston 4 and the open end 2a of the housing 2. The spring means 9 is selected from a group consisting of a tension spring, a torsion spring and a bending spring. Accordingly, when the piston 4 is forced toward the barrier layer 6 and then released, the piston 4 can generate restoring force to enable the piston 4 returned to cause a negative-pressure source.

Figure 4A:
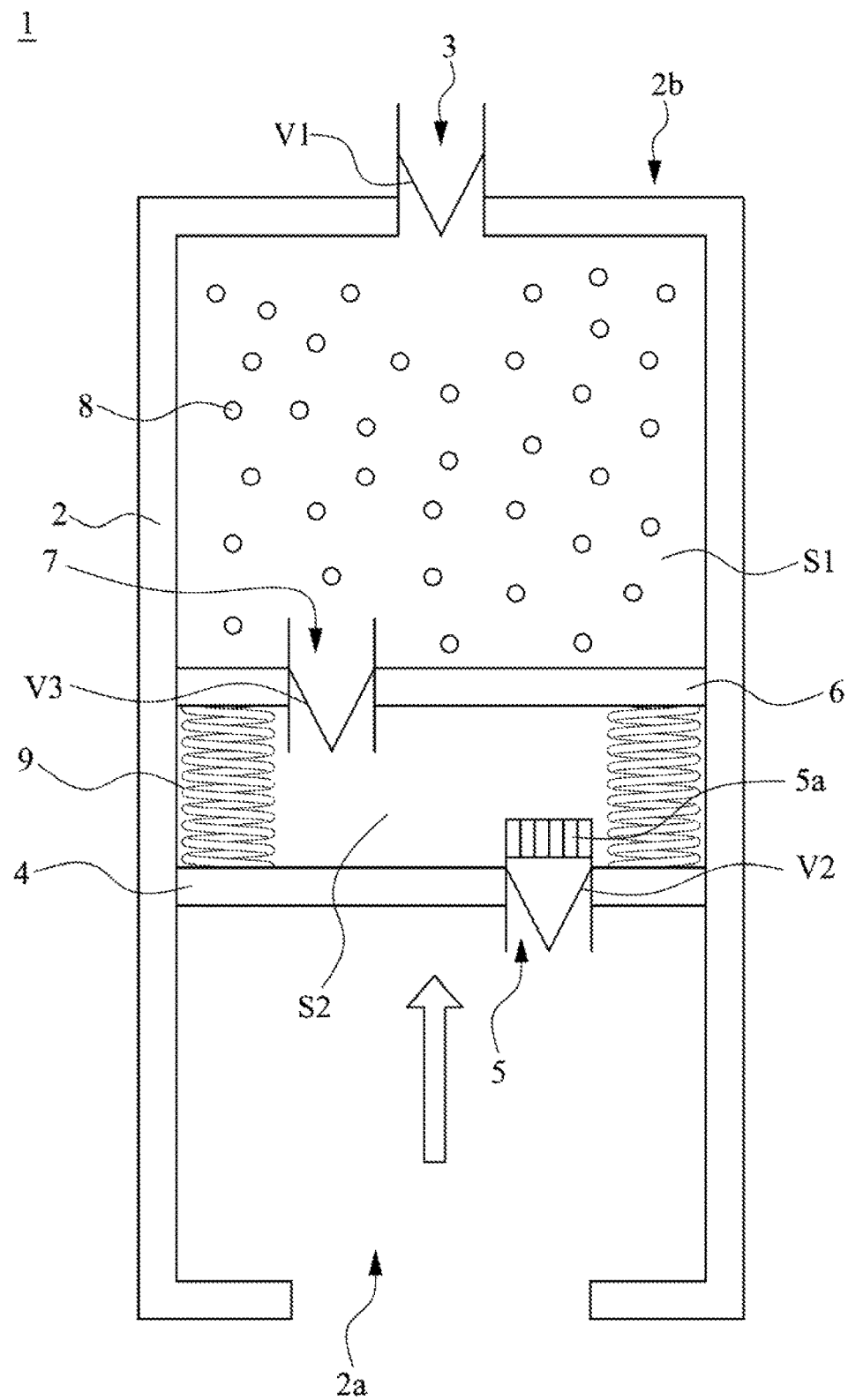
FIG. 4a and FIG. 4b illustrate the principle of a negative-pressure device for forming a negative-pressure source in accordance with another embodiment of the present disclosure.
Figure 4B:
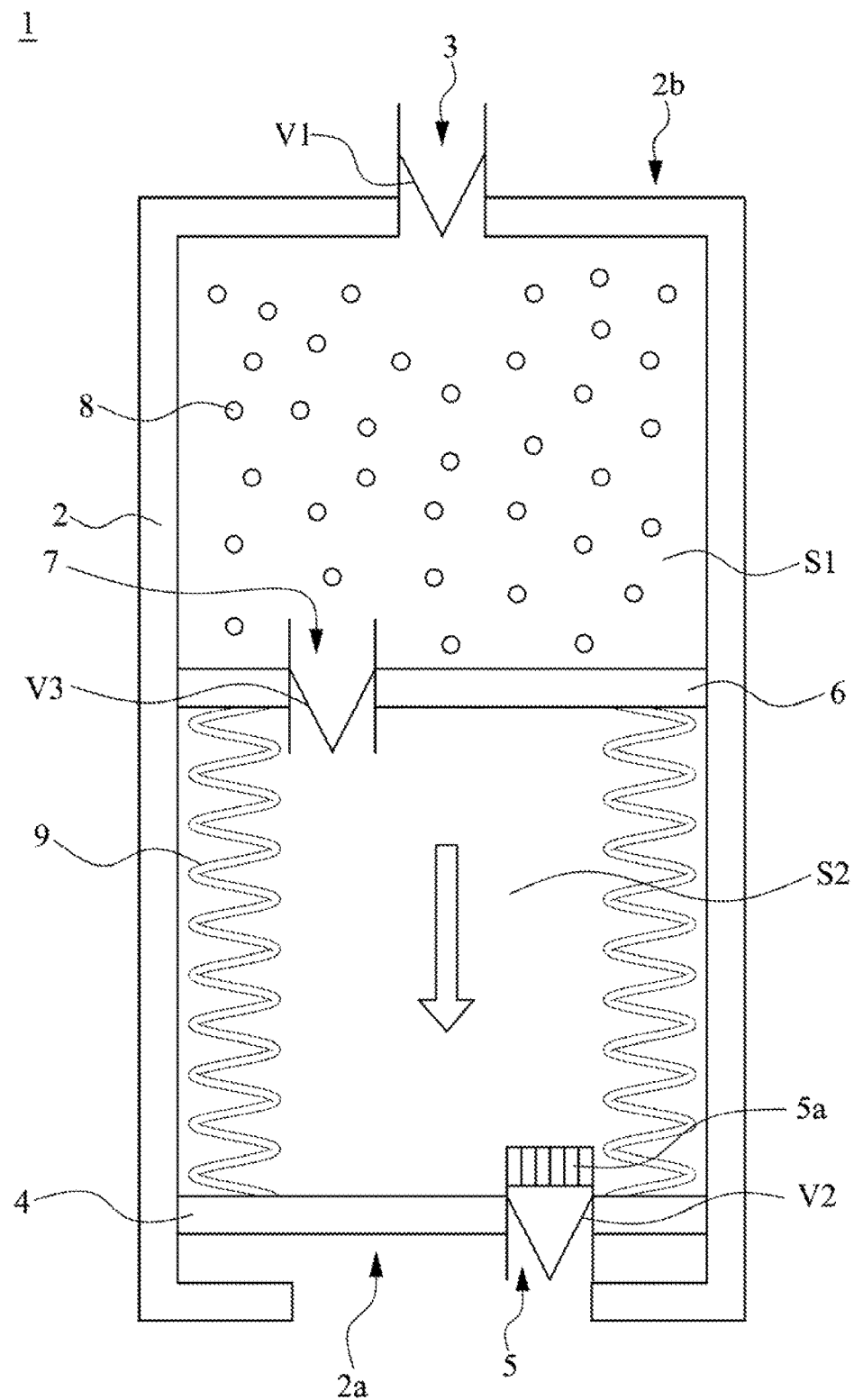

Referring to FIG. 4a and FIG. 4b, in a portable negative-pressure device of another preferred embodiment of the present disclosure, the spring means 9 is disposed between the piston 4 and the barrier layer 6. The spring means 9 is selected from a group consisting of a compression spring, a torsion spring and a bending spring. When the piston 4 is forced toward the barrier layer 6 and then released, the piston 4 will generate restoring force to enable the piston 4 returned to cause a negative-pressure source.

In a portable negative-pressure device of another preferred embodiment of the present disclosure, the air-permeable waterproof structure 5a comprises an air-permeable waterproof film or liquid absorbing particles. The compressed gas can pass through the pores of the air-permeable waterproof film or the gap of the liquid absorbing particles and discharged by the second check valve V2. When the second collection chamber S2 starts to collect the exudates, the exudates is absorbed by the liquid absorbing particles without leaking and does not pass through the pores of the air-permeable waterproof film.

Figure 5A:
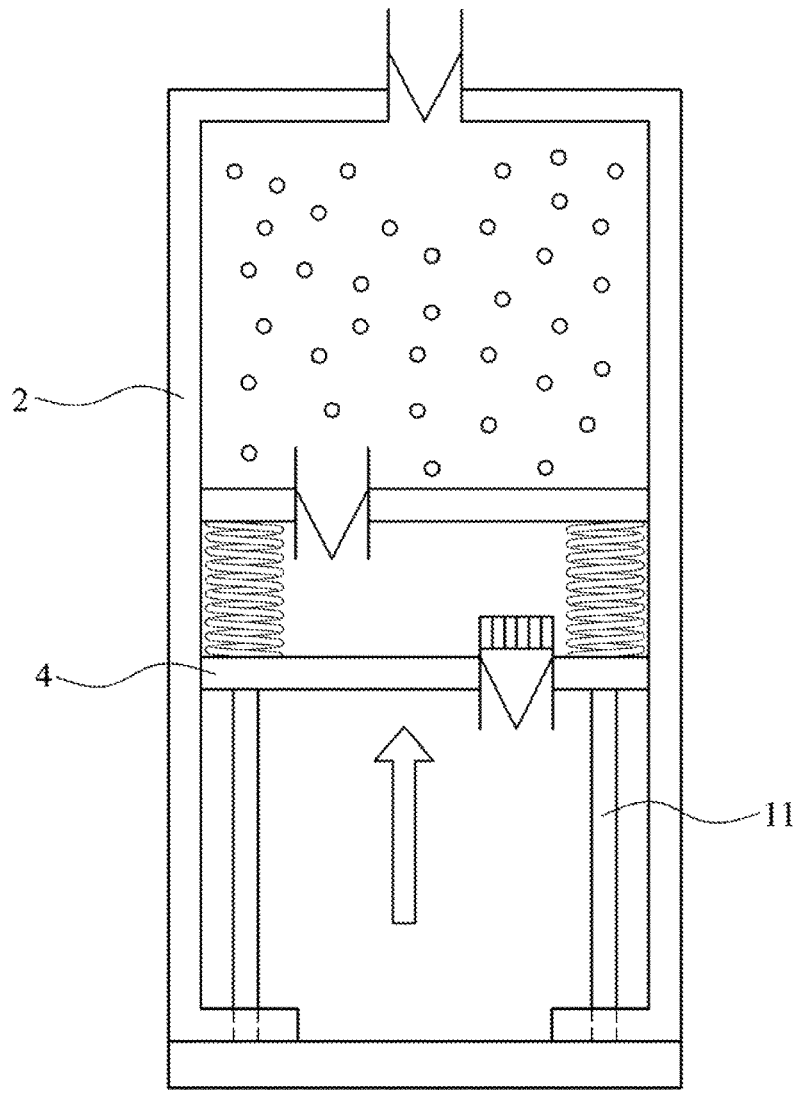
FIG. 5a and FIG. 5b show the cross-sectional prospective view of a negative-pressure device including an auxiliary tool in accordance with another embodiment of the present disclosure.
Figure 5B:
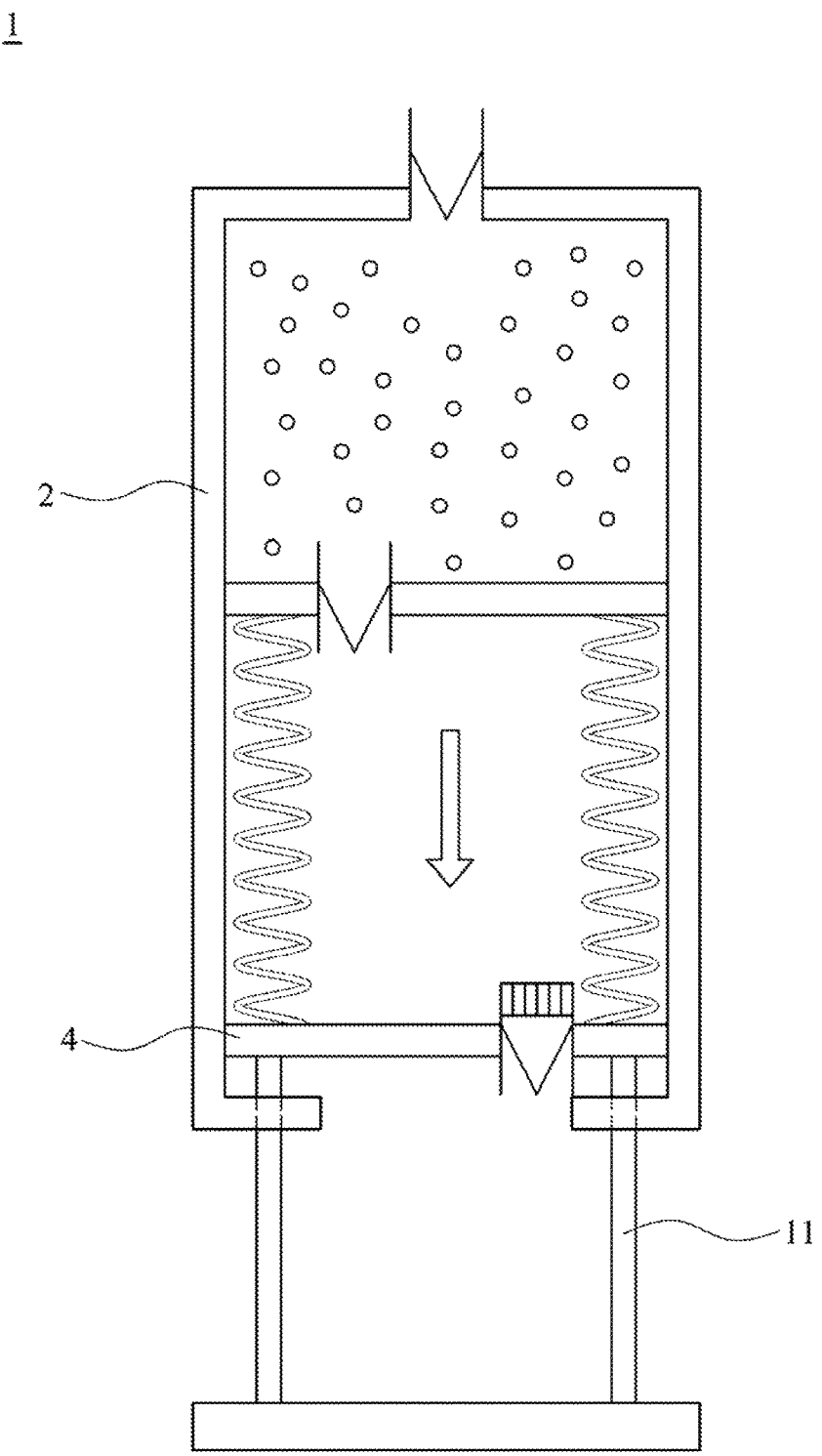

Referring to FIG. 5a and FIG. 5b, in a portable negative-pressure device of another preferred embodiment of the present disclosure, the portable negative-pressure device 1 further comprises an auxiliary tool 11 removably disposed at an edge of the housing 2 for forcing the piston 4 sliding toward the barrier layer 6 to cause a negative-pressure source. The auxiliary tool 11 can be housed at one end of the housing 2 after using.

Figure 6:
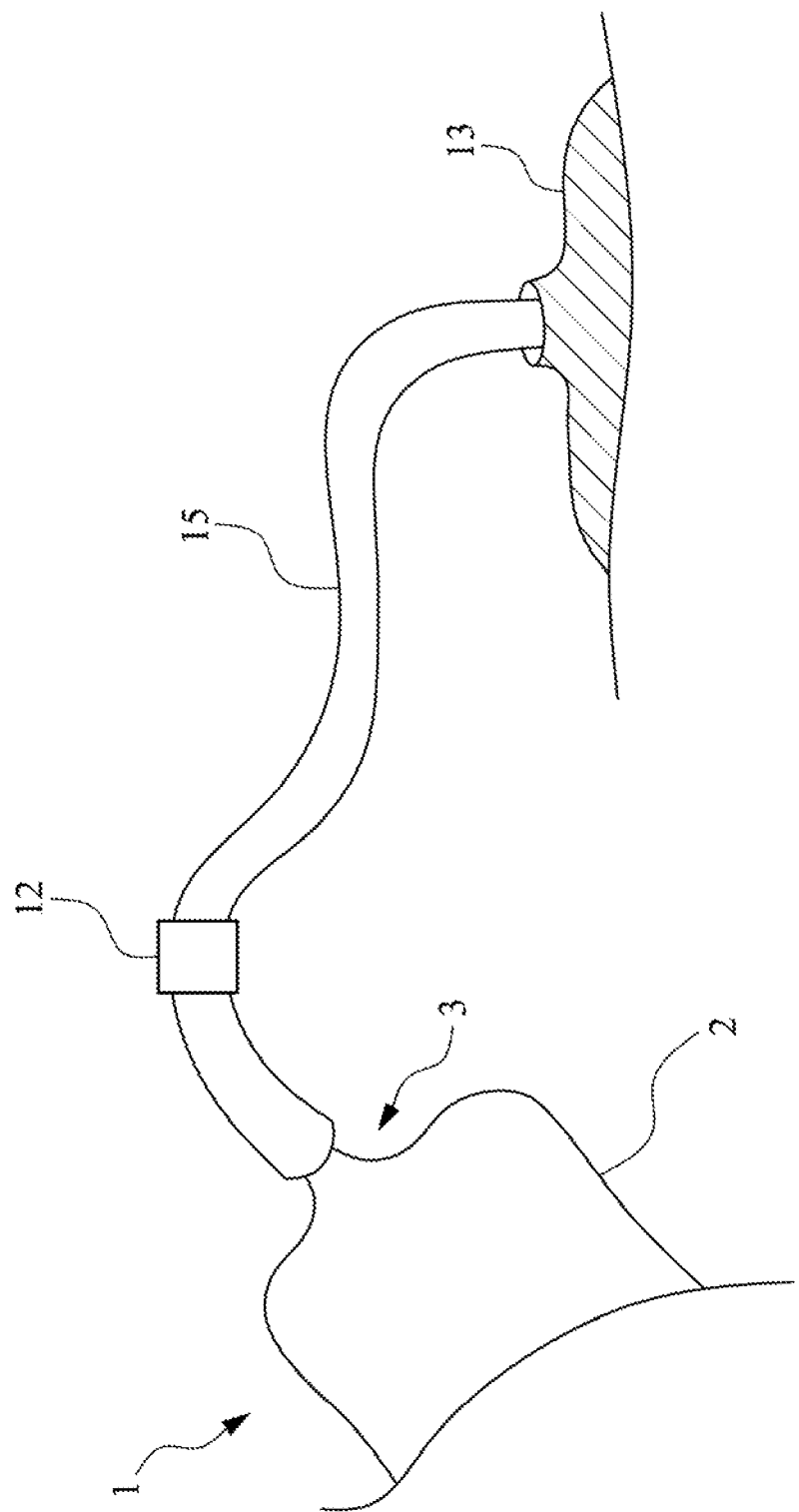
FIG. 6 illustrates the distribution of a pressure regulator and a delivery tube of a negative-pressure device in accordance with another embodiment of the present disclosure.

Referring to FIG. 6, in a portable negative-pressure device of another preferred embodiment of the present disclosure, the portable negative-pressure device 1 further comprises a pressure regulator 12 at the delivery tube 15 between the exudates inlet 3 and the negative-pressure wound dressing 13 for obtaining more appropriate negative pressure depended on the situation of the exudates, and avoiding discomfort of the wound.

In a portable negative-pressure device of another preferred embodiment of the present disclosure, the pressure regulator 12 is integrated at the exudates inlet 3.

Figure 7:
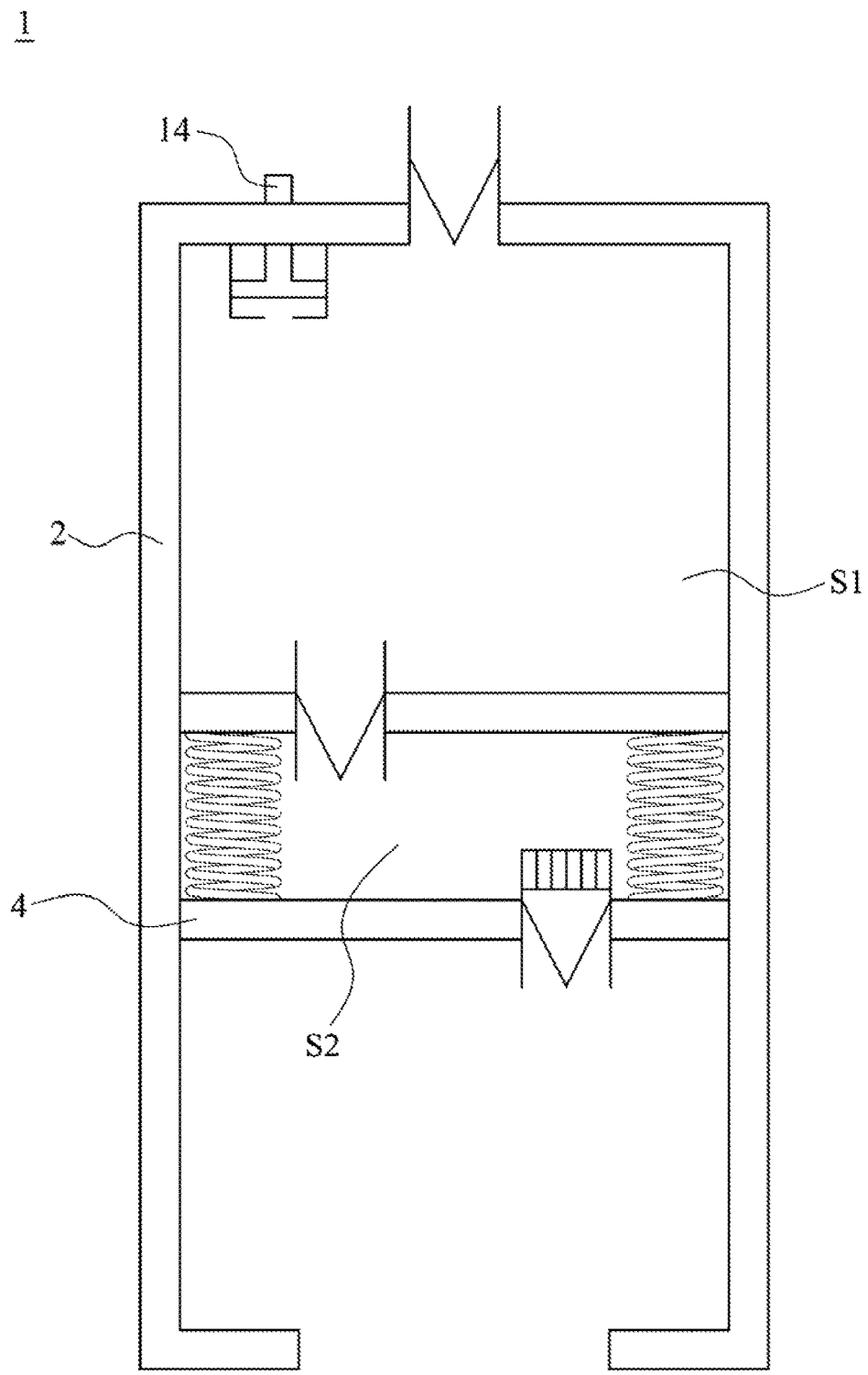
FIG. 7 shows the cross-sectional prospective view of a negative-pressure device including a pressure sensor in accordance with another embodiment of the present disclosure.

Referring to FIG. 7, in a portable negative-pressure device of another preferred embodiment of the present disclosure, the portable negative-pressure device 1 further comprises a pressure sensor 14, which is disposed at a side of the housing 2, interconnecting the first collection chamber S1 and the second collection chamber S2 to indicate the degree of the negative pressure. The pressure sensor 14, for example, may have a threshold. When the pressure in the portable negative-pressure device 1 rises to a threshold as the exudates increase in use, the pressure sensor 14 may instruct the user to push the piston 4 again to compress the second collection chamber S2 to maintain appropriate degree of negative pressure.

While the disclosure has been described by way of example(s) and in terms of the preferred embodiment(s), it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A portable negative-pressure device for a negative-pressure wound dressing, comprising:
    a housing having an open end and a closed end, wherein the closed end has an exudates inlet having a first check valve and connected to the negative-pressure wound dressing via a delivery tube;
    a piston slidably disposed at the open end of the housing, the piston having an exhaust port having a second check valve and an air-permeable waterproof structure;
    a barrier layer disposed in the housing to form with the closed end a first collection chamber having a fixed volume, and to form a second collection chamber having a variable volume varied with a position of the piston, wherein the barrier layer has a passage with a third check valve connected to the first collection chamber and the second collection chamber, and the first collection chamber comprises a first absorbent material, wherein the exudate inlet is configured to collect exudates to the first collection chamber, and the first collection chamber and the second collection chamber are configured to collect the exudates; and
    a spring means disposed to the piston and configured to form the second collection chamber as a pressure-reducing region from the compression and resilience back of the piston against the second collection chamber.

2. The portable negative-pressure device of claim 1, wherein the first collection chamber comprises a porous conduit which is connected to the exudates inlet and extended to the first collection chamber, so as to uniformly distribute the exudates from the dressing to the first absorbent material of the first collection chamber.

3. The portable negative-pressure device of claim 2, wherein the porous conduit comprises a manifold structure.

4. The portable negative-pressure device of claim 1, wherein the second collection chamber comprises a second absorbent material for further absorbing the exudates.

5. The portable negative-pressure device of claim 4, wherein the first absorbent material and the second absorbent material are independently selected from a group consisting of sodium polyacrylate, polyacrylamide, polyvinyl alcohol and polyoxyethylene.

6. The portable negative-pressure device of claim 1, wherein the spring means is one selected from a group consisting of a tension spring, a compression spring, a torsion spring and a bending spring.

7. The portable negative-pressure device of claim 1, wherein one end of the spring means is disposed on the piston and another end is connected to the open end of the housing.

8. The portable negative-pressure device of claim 1, wherein one end of the spring means is disposed on the piston and another end is connected to the barrier layer.

9. The portable negative-pressure device of claim 1, wherein the air-permeable waterproof structure comprises an air-permeable waterproof film or liquid absorbing particles.

10. The portable negative-pressure device of claim 1, further comprising an auxiliary tool removably disposed at an edge of the housing for pushing the piston to slide toward the barrier layer.

11. The portable negative-pressure device of claim 1, further comprising a pressure regulator at the delivery tube between the exudates inlet and the negative-pressure wound dressing.

12. The portable negative-pressure device of claim 11, wherein the pressure regulator is integrated at the exudates inlet.

13. The portable negative-pressure device of claim 1, further comprising a pressure sensor, which is disposed at a side of the housing, interconnecting the first collection chamber and the second collection chamber to indicate the degree of the negative pressure.

* * * * *